United States Patent [19]

Altenschöpfer et al.

[11] Patent Number: 4,465,612

[45] Date of Patent: Aug. 14, 1984

[54] PROCESS FOR CLEANING AND MAINTAINING THE INTERIOR SURFACES OF A MECHANICAL DISHWASHER

[75] Inventors: Theodor Altenschöpfer, Dusseldorf; Klaus Schuman, Erkrath, both of Fed. Rep. of Germany

[73] Assignee: Henkel Kommanditgesellschaft auf Aktien, Duesseldorf, Fed. Rep. of Germany

[21] Appl. No.: 480,091

[22] Filed: Mar. 29, 1983

Related U.S. Application Data

[63] Continuation-in-part of Ser. No. 226,145, Jan. 19, 1981, Pat. No. 4,392,977.

[30] Foreign Application Priority Data

Nov. 4, 1982 [DE] Fed. Rep. of Germany ....... 3240688

[51] Int. Cl.$^3$ .......................... C11D 1/72; C11D 7/50
[52] U.S. Cl. ....................................... 252/143; 134/41; 134/42; 252/142; 252/146; 252/171; 252/173; 252/174.19; 252/174.21
[58] Field of Search ............... 252/142, 143, 148, 146, 252/DIG. 10, 173, 171, 174.19, 174.21, DIG. 14, DIG. 2; 134/42, 41

[56] References Cited

U.S. PATENT DOCUMENTS

| | | | |
|---|---|---|---|
| 3,775,330 | 11/1973 | Batka et al. | 252/174.19 |
| 3,779,934 | 12/1973 | Altenschopfer et al. | 252/142 |
| 3,941,713 | 3/1976 | Dawson et al. | 252/142 |
| 3,969,134 | 7/1976 | Batka et al. | 134/26 |
| 4,152,305 | 5/1979 | Berghausen | 252/523 |
| 4,172,044 | 10/1979 | Zeidler et al. | 252/142 |
| 4,239,552 | 12/1980 | Perner et al. | 134/28 |

*Primary Examiner*—P. E. Willis, Jr.
*Attorney, Agent, or Firm*—Ernest G. Szoke; Nelson Littell, Jr.

[57] ABSTRACT

A process for manual and mechanical cleaning and maintaining the interior surfaces of an unloaded mechanical dishwasher machine as such consisting essentially of applying to the interior of the mechanical dishwasher in an unloaded condition a liquid, acid-reacting cleaning and maintenance composition consisting essentially of:

(a) from 5% to 50% by weight of an acid having from 2 to 6 carbon atoms selected from the group consisting of alkanoic acids, hydroxy substituted alkanoic acids, alkane polycarboxylic acids and hydroxy substituted alkane polycarboxylic acids, (b) from 3% to 20% by weight of a water-soluble alkane polyol, (c) from 0.1% to 10% by weight of a low-sudsing nonionic tenside, (d) from 0 to 5% by weight of customary additives selected from the group consisting of odorants, dyes, dissolving intermediaris and corrosion inhibitors, (e) from 0 to 30% by weight of a water-miscible alkanol havig from 2 to 4 carbon atoms, and (f) the remainder to 100% by weight of water, where the amount of water is at least 25% by weight, based on the total weight of the composition.

12 Claims, No Drawings

PROCESS FOR CLEANING AND MAINTAINING THE INTERIOR SURFACES OF A MECHANICAL DISHWASHER

This application is a continuation-in-part of Ser. No. 226,145, Filed Jan. 19, 1981, now U.S. Pat. No. 4,392,977.

BACKGROUND OF THE INVENTION

In the area of door sealings, hose connections and low water zones of mechanical dishwashers, that is, where the surfaces of the interior of the dishwasher are not exposed to the direct and intensive operating pressure spray of the cleaning liquor, soil is frequently deposited in the course of time. This soil consists mainly of finely-divided fatty food residues.

Occasional unavoidable troubles in the ionexchange system of the dishwasher water supply, which serve to soften the water used, or the consistent underdosing of the dishwasher detergents by the user also cause increasingly deposits of a mixture of calcium from hard water and residues of the detergents on the inner surfaces of the machines.

Partly so-called "tempering colors" are formed, as rainbow-colored discolorations of refined steel parts of the dishwasher are called.

These deposits represent an undesired nutrient soil for rotting processes, which manifest themselves by an unpleasant odor, particularly when the dishwasher is opened after it has not been used for a long time. Beyond that, hose connections and sealing materials, particularly at the door, are damaged by prolonged action of these soil deposits.

The commercial powdered alkaline dishwasher detergents or acid clear rinse agents are not suitable for cleaning the so-called "problem zones" of dishwashers where soil is particularly likely to be deposited. These dishwasher detergents are dosed into the washing and rinsing cycle of the dishwashers and are dissolved therein; however, the soiled regions either are not touched at all or only too briefly by them. So, soil is depositing in the interior of the dishwashers in spite of the use of these detergents. It is, therefore, necessary to clean these special zones manually. The detergents used for cleaning the dishes are unsuitable for this purpose, since they irritate the skin. Commercial cleansers for hard surfaces are not suitable either for these special applications, since they contain generally high-sudsing tensides or surface-active compounds whose residues can lead to various troubles in dishwashers.

Object of the Invention

An object of the present invention is to develop a process for the manual cleaning and maintaining the interior surfaces of mechanical dishwasher as such employing a liquid composition.

Another object of the present invention is the development of a process for cleaning and maintaining the interior surfaces of a mechanical dishwasher as such consisting essentially of conducting the normal cleaning program of the mechanical dishwasher in an unloaded condition in the presence of a liquid, acid-reacting cleaning and maintenance composition consisting essentially of (a) from 5% to 50% by weight of an acid having from 2 to 6 carbon atoms selected from the group consisting of alkanoic acids, hydroxy substituted alkanoic acids, alkane polycarboxylic acids and hydroxy substituted alkane polycarboxylic acids, (b) from 3% to 20% by weight of a water-soluble alkane polyol, (c) from 0.1% to 10% by weight of a low-sudsing nonionic tenside, (d) from 0 to 5% by weight of customary additives selected from the group consisting of odorants, dyes, dissolving intermediaries and corrosion inhibitors, (e) from 0 to 30% by weight of a water-miscible alkanol having from 2 to 4 carbon atoms, and (f) the remainder to 100% by weight of water, where the amount of water is at least 25% by weight, based on the total weight of the composition.

These and other objects of the invention will become more apparent as the description thereof proceeds.

Description of the Invention

The present invention concerns the use of a liquid, acid-reacting composition, consisting essentially of:

(a) from 5% to 50% by weight of an acid having from 2 to 6 carbon atoms selected from the group consisting of alkanoic acids, hydroxy substituted alkanoic acids, alkane polycarboxylic acids and hydroxy substituted alkane polycarboxylic acids, (b) from 3% to 20% by weight of a water-soluble alkane polyol, (c) from 0.1% to 10% by weight of a low-sudsing nonionic tenside, (d) from 0 to 5% by weight of customary additives selected from the group consisting odorants, dyes, dissolving intermediaries and corrosion inhibitors, (e) from 0 to 30% by weight of a water-miscible alkanol having from 2 to 4 carbon atoms, and (f) the remainder to 100% by weight of water, where the amount of water is at least 25% by weight, based on the total weight of the composition, for cleaning and maintaining the interior surfaces and the hose connections and sealing parts of the interior of an unloaded mechanical dishwasher machine as such, whereby the liquid composition is (i) added into the interior of the unloaded dishwasher machine and subsequently the normal cleaning program of the dishwasher machine is operated, and/or (ii) applied manually on the problem zones of the interior of the open unloaded dishwasher machine. The composition as employed in the care and maintaining of the interior surfaces of a mechanical dishwasher is characterized in that it contains:

from 5% to 50%, preferably from 12% to 25%, by weight of a water-soluble organic monocarboxylic acid or polycarboxylic acid with 2 to 6 carbon atoms in the molecule, substituted, optionally, by hydroxy groups, from 3% to 20%, preferably 5% to 12%, by weight of a water-soluble polyhydric alcohol, from 0.1% to 10%, preferably 1% to 5%, be weight of a low-sudsing nonionic tenside, and from 0 to 5%, preferably 0.1% to 4.5%, by weight of odorants, dyes, dissolving intermediaries and/or inhibitors, related to the total weight of an aqueous or aqueous-alcoholic solution.

More particularly, the present invention relates to a process for manual and mechanical cleaning and maintaining the interior surfaces of an unloaded mechanical dishwasher machine as such consisting essentially of applying to the interior of the mechanical dishwasher machine in an unloaded condition a liquid, acid-reacting cleaning and maintenance composition consisting essentially of:

(a) from 5% to 50% by weight of an acid having from 2 to 6 carbon atoms selected from the group consisting of alkanoic acids, hydroxy substituted alkanoic acids, alkane polycarboxylic acids and hydroxy substituted alkane polycarboxylic acids, (b) from 3% to 20% by weight of a water-soluble alkane polyol, (c) from 0.1% to 10% by weight of a low-sudsing nonionic tensides, (d) from 0 to 5% by weight of customary additives selected from the group consisting of odorants, dyes, dissolving intermediaries and corrosion inhibitors, (e) from 0 to 30% by weight of a water-miscible alkanol having from 2 to 4 carbon atoms, and (f) the remainder to 100% by weight of water, where the amount of water is at least 25% by weight, based on the total weight of the composition.

In addition to at least 25% by weight of water, the composition used in the invention can contain preferably from 15% to 20% by weight of a water-miscible alkanol having from 2 to 4 carbon atoms, such as ethanol, propanol, butanol and preferably isopropanol.

The water-soluble organic monocarboxylic or polycarboxylic acids with 2 to 6 carbon atoms in the molecule, substituted if necessary by hydroxy groups, consist primarily of alkanoic acids, hydroxyalkanoic acids, alkane polycarboxylic acids and hydroxyalkane polycarboxylic acids. In addition to acetic acid, preferably polycarboxylic acids which have a K value of $<10^{-6}$, related to the first dissociation stage are employed. These are, for example, adipic acid, succinic acid, tartaric acid, malic acid, glutaric acid, and preferably citric acid. Mixtures of these acids can also be used.

The water-soluble polyhydric alcohols are preferably water-soluble alkane polyols having from 2 to 6 carbon atoms and from 2 to 3 hydroxyls in the molecule, such as ethylene glycol, propylene glycol, dipropylene glycol and preferably glycerin.

In order to increase the detergent power, known low-sudsing nonionic tensides are used which are used, too, as components of detergents for the mechanical cleaning of dishes. Suitable are oxide adducts onto higher molecular weight propylene glycols with molecular weights of 900 to 4,000, as well as adducts of 1 to 10 mols of ethylene oxide and 1 to 7 mols of propylene oxide onto higher molecular weight fatty alcohols with 10 to 20, preferably 12 to 18, carbon atoms in the molecule, or mixtures thereof, as well as synthetic alcohols of the chain length $C_{12}$–$C_{18}$, produced by oxosynthesis, and corresponding alkylene oxide adducts on nonylphenols. Preferred are the biodegradable adducts of ethylene oxide and propylene oxide onto higher molecular weight fatty alcohols, particularly the addition product of 2 to 5 mols of ethylene oxide and 2 to 5 mols of propylene oxide onto a mixture of $C_{12}$–$C_{18}$ fatty alcohols.

Apart from dyes and odorants, small amounts of about 0.1 to 4.5% by weight of customary dissolving intermediaries for the tensides and/or odorants can be added, e.g., $C_1$–$C_3$-alkylbenzene sulfonates, especially cumenesulfonates, as well as corrosion inhibitors, e.g., a condensation product of aldehydes and amines in a acid medium known under the name of Rodin 58 ® by Gerhard Bollardin GmbH, Cologne, Germany.

The compositions used according to the invention are added to the unloaded dishwasher in amounts of from 50 to 400 ml, i.e. in concentrations of 5 to 40, preferably 10 to 25, gm/liter in certain intervals, for example, once or twice a month, using a full program of the washing and the rinsing cycle, which means, that the concentrates are left there at least for about five minutes at an elevated temperature of about 25° to 60° C. However they can also be used for cleaning the soiled regions manually in undiluted form with the aid of an absorbing substrate like a sponge or a cloth by application to the open unloaded disheasher without starting the cleaning cycles. Preferably a manual pretreatment is combined with the mechanical cleaning process using the conventional dishwasher cleaning program.

The liquid, acid cleaning and maintenance compositions according to the invention dissolve and remove both the fatty food residues and calcium and detergent residues in dishwashers. Tempering colors too disappear on rubbing. Due to their content of polyvalent alcohols, premature drying of the agent is prevented. This way not only rubber and plastic seals or connections are kept soft and elastic, but stubborn stains are softened and can be easily wiped off, due to the delayed drying.

The following examples illustrate compositions used in the invention and the invention in more detail without being limitative thereof.

EXAMPLE 1

| Percent By Weight | |
|---|---|
| 1.5 | An adduct of 2 mols of ethylene oxide and 4 mols of propylene oxide onto a technical mixture of $C_{12}$–$C_{18}$ fatty alcohols, |
| 15.0 | Citric acid |
| 8.0 | Glycerine, anhydrous |
| 20.0 | Isopropanol |
| 4.0 | Dipropylene glycol |
| 0.15 | An odorant |
| 50.25 | Water. |

EXAMPLE 2

The following composition was mixed together:

| Percent By Weight | |
|---|---|
| 3.0 | A 1:1 mixture of an adduct of 2 mols of ethylene oxide and 4 mols of propylene oxide onto a technical mixture of $C_{12}$–$C_{18}$ fatty alcohols and an adduct of 5 mols of ethylene oxide and 4 mols of propylene oxide onto a technical mixture of $C_{12}$–$C_{18}$ fatty alcohols, |
| 15.0 | Citric acid |
| 3.0 | Acetic acid |
| 10.0 | Ethylene glycol |
| 22.0 | Isopropanol |
| 6.5 | Corrosion inhibitor, "Rodine 58"$^{(R)}$ |
| 40.5 | Water. |

EXAMPLE 3

| Percent By Weight | |
|---|---|
| 3.5 | An adduct of 4 mols of ethylene oxide and 2 mols of propylene oxide onto a technical $C_{12}$–$C_{18}$ fatty alcohol mixture, |
| 6.0 | Tartaric acid |
| 3.0 | Adipic acid |
| 2.0 | Succinic acid |
| 5.0 | Glutaric acid |
| 2.0 | Citric acid |
| 10.0 | Glycerine anhydrous |
| 18.0 | Ethanol |
| 0.2 | Odorant |
| 50.3 | Water. |

EXAMPLE 4

Cleaning Effect

The following test arrangement was used to determine the cleaning effect of the manually applied compositions of the invention on rubber or plastic parts of dishwashers:

A plastic test plate of 26×28 cm was employed. Two grams of an artificial soil consisting of a mixture of soot, machine oil, triglycerides of saturated fatty acids and low boiling aliphatic hydrocarbons were applied evenly to the plates by means of an applicator.

A plastic sponge was saturated with 12 ml of the detergent compositions according to Examples 1 to 3 to be tested, and moved mechanically over the test area. After six wiping movements, the cleaned test area was held under running water and the loose soil was removed. The cleaning effect, that is, the whiteness of the plastic surface thus cleaned, was measured with a photoelectric colorimeter LF 90 (Dr. B. Lange). The original clean white plastic surface was used as a white standard. In the measurement, this clean surface was adjusted to be 100% and the artificially soiled surface was adjusted to be 0%. The indicated values of the cleaned plastic surface must be considered as percent cleaning effect (% CE). These are mean values from four determinations. With tap water, a mean value of 21% CE was obtained.

| Example | % CE |
|---|---|
| 1 | 71 |
| 2 | 77 |
| 3 | 75 |

EXAMPLE 5

The result of the mechanical application of the detergent compositions according to the invention for cleaning the interior of dishwashers was determined in the form of the calcium dissolving power and of the cleaning power. To this end one of the compositions according to Examples 1 to 3, at a rate of 250 ml, was put into the cleaning cycle of a commercial dishwasher Model Miele G 540, with a water content of 10.0±0.5 l and a maximum washing temperature of 55° C.±3° C.

Calcium Dissolving Power:

Glass plates 6×12 were covered evenly with a layer of 5 gm of a mixture of:

| Grams | |
|---|---|
| 80 | Calcium carbonate |
| 7 | Sodium metasilicate, anhydrous |
| 4 | Magnesium carbonate-hexahydrate |
| 2 | Gelatin |
| 60 | Water | and dried for one and half hours at 80° C. This resulted in a stable "calcium deposit". Four glass plates each were washed with one of the agents according to Examples 1 to 3 in the dishwasher. The mean percentual removal of the calcium deposit (calcium dissolving power) was determined by titrimetric determination of the residual amounts of $Ca^{++}$- and $Mg^{++}$-ions. The calcium dissolving power effected solely with water of 55° C. by mechanical removal in the dishwasher was 30%.

| Example | % Calcium Dissolving Power |
|---|---|
| 1 | 75 |
| 2 | 81 |
| 3 | 69 |

Cleaning Power:

Thirty grams of soil consisting of:

| Grams | |
|---|---|
| 100 | Margarine |
| 50 | Raw egg (white and yellow) |
| 50 | Defrosted frozen spinach |
| 100 | Drinking milk, 1.5% fat content |
| 100 | Food grade rolled oats |
| 280 | Mashed potatoes |
| 400 | Brown gravy | were applied in stripes on refined steel surfaces of the interior of three dishwashers. Model Miele G 540, by means of a brush and left drying for twenty hours at room temperature. Then one of the compositions, each according to Examples 1 to 3, was put into the cleaning cycles of the unloaded dishwashers and the latter started as usual. Subsequently the result was judged by three test persons. The original, new refined steel inner surface was graded as 10 (absolutely clean) and the refined steel surfaces obtained after soiling as 0. With pure water treatment at 55° C., a cleaning power grade of 5.5 was obtained.

| Example | Cleaning Power |
|---|---|
| 1 | 8.5 |
| 2 | 9.5 |
| 3 | 8.0 |

EXAMPLE 6

A brand new commercial dishwashing machine with inside parts of stainless steel was installed in a four-person household and put into regular use. This meant at least one complete washing cycle per day with the kitchen utensils, dishes and cutlery involved in the cooking and consumption of the usual meals. After four months of regular use, the state of the machine was inspected by three experienced persons. Fatty food residues were noticed in the region of the rubber gasket of the door of the machine. In addition, residues of the detergent had deposited on the rubber gaskets. Further there had formed on a part of the stainless steel surfaces of the inner drum of the dishwashing machine rainbow color discolorations, so-called "tempering colors". It was decided to subject the machine in this state to a maintenance cleaning process.

For this purpose, a slightly moist cloth of synthetic sponge was first impregnated with a few cc of the concentrate according to Example 1. Then the edges of the rubber gasket on the machine door were rubbed therewith, a part of the dirt being taken up by the sponge cloth or the existing coating was loosened. Thereafter the program selector of the machine was set on "Start Cleaning Cycle"; subsequently 200 ml of the composition according to Example 1 was poured out into the interior of the unloaded machine, the machine door closed, and the cleaning program set in motion at 65° C. At the end of the cleaning program, when the machine stopped, the machine door was opened, and the appearance of the interior of the unloaded and nearly dry machine was judged by the three test persons. The state of the machine was unanimously rated as "good as new." This evaluation referred both to the internal surfaces of stainless steel and to the aspect of the rubber gasket of the door.

The dishwasher, afterwards, was loaded with dirty kitchen utensils and used as customary with an alkaline-reacting powdered dishwashing agent and an acid-reacting liquid clear-rinse agent for a further new period of nearly a month.

It must be assured, that there is no contact between the acid-reacting cleaning and maintaining composition of the present invention and the alkaline-reacting dishwashing agent because of the possible development of poisonous gases resulting from the chlorine content of most dishwashing agents.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A process for manual and mechanical cleaning and maintaining the interior surfaces of an unloaded mechanical dishwasher machine as such consisting essentially of applying to the interior of the mechanical dishwasher machine in an unloaded condition a liquid, acid-reacting cleaning and maintenance composition consisting essentially of:
   (a) from 5% to 50% by weight of an acid having from 2 to 6 carbon atoms selected from the group consisting of alkanoic acids, hydroxy substituted alkanoic acids, alkane polycarboxylic acids and hydroxy substituted alkane polycarboxylic acids,
   (b) from 3% to 20% by weight of a water-soluble alkane polyol having from 2 to 6 carbon atoms and from 2 to 3 hydroxyls in the molecule,
   (c) from 0.1% to 10% by weight of a low-sudsing nonionic tenside,
   (d) from 0 to 5% by weight of customary additives selected from the group consisting of odorants, dyes, dissolving intermediaries and corrosion inhibitors,
   (e) from 0 to 30% by weight of a water-miscible alkanol having from 2 to 4 carbon atoms, and
   (f) the remainder to 100% by weight of water, where the amount of water is at least 25% by weight,
   based on the total weight of the composition.

2. The process of claim 1 wherein said low-sudsing nonionic tenside is the addition product of 2 to 5 mols of ethylene oxide and 2 to 5 mols of propylene oxide onto a mixture of $C_{12}$-$C_{18}$ fatty alcohols.

3. The process of claim 1 wherein said liquid, acid-reacting cleaning and maintenance composition is applied manually on the problem zones of the interior and on the sealing materials of said unloaded open dishwasher machine with the aid of an absorbing substrate.

4. The process of claim 1 wherein said liquid, acid-reacting cleaning and maintenance composition is added in amounts of 5 to 40 gm/liter into the interior of said unloaded dishwasher machine before operating the normal cleaning program of the dishwasher machine.

5. The process of claim 1 wherein said liquid, acid-reacting cleaning and maintenance composition in a first step is applied manually on the problem zones of the interior and on the sealing materials of said unloaded open dishwasher machine with the aid of an absorbing substrate and in a second step said liquid, acid-reacting cleaning and maintenance composition is added into the interior of said unloaded dishwasher machine before operating the normal cleaning program of the dishwasher machine.

6. The process of claim 4 wherein said normal cleaning program is conducted at a temperature of about 25° C. to 65° C.

7. The process of claim 5 wherein said normal cleaning program is conducted at a temperature of about 25° C. to 65° C.

8. The process of claim 4 wherein said liquid, acid-reacting cleaning and maintenance composition is present for at least about five minutes during the normal cleaning program of said unloaded dishwasher machine.

9. The process of claim 5 wherein said liquid, acid-reacting cleaning and maintenance composition is present for at least about five minutes during the normal cleaning program of said unloaded dishwasher machine.

10. The process of claim 6 wherein said liquid, acid-reacting cleaning and maintenance composition is present for at least about five minutes during the normal cleaning program of said unloaded dishwasher machine.

11. The process of claim 7 wherein said liquid, acid-reacting cleaning and maintenance composition is present for at least about five minutes during the normal cleaning program of said unloaded dishwasher machine.

12. The process of claim 1 conducted once or twice a month.

* * * * *